(12) United States Patent
Usuki et al.

(10) Patent No.: US 10,744,071 B2
(45) Date of Patent: Aug. 18, 2020

(54) DENTAL ALGINATE IMPRESSION MATERIAL

(71) Applicant: GC Corporation, Shizuoka (JP)

(72) Inventors: Daisuke Usuki, Tokyo (JP); Naofumi Niizeki, Tokyo (JP); Tomohiro Kumagai, Tokyo (JP)

(73) Assignee: GC Corporation, Shizuoka (JP)

( * ) Notice: Subject to any disclaimer, the term of this patent is extended or adjusted under 35 U.S.C. 154(b) by 117 days.

(21) Appl. No.: 16/084,631

(22) PCT Filed: Dec. 1, 2016

(86) PCT No.: PCT/JP2016/085803
§ 371 (c)(1),
(2) Date: Sep. 13, 2018

(87) PCT Pub. No.: WO2017/163491
PCT Pub. Date: Sep. 28, 2017

(65) Prior Publication Data
US 2019/0076336 A1    Mar. 14, 2019

(30) Foreign Application Priority Data
Mar. 22, 2016 (JP) ................................. 2016-056593

(51) Int. Cl.
*A61K 6/10* (2006.01)
*A61K 6/90* (2020.01)

(52) U.S. Cl.
CPC ...................................... *A61K 6/90* (2020.01)

(58) Field of Classification Search
CPC ....................................................... A61K 6/90
See application file for complete search history.

(56) References Cited

U.S. PATENT DOCUMENTS

| | | | | |
|---|---|---|---|---|
| 2,657,971 A | * | 11/1953 | Lochridge | A61K 6/90 106/38.51 |
| 2,936,242 A | * | 5/1960 | Brauer | A61K 6/78 106/35 |
| 5,505,771 A | | 4/1996 | Chihara et al. | |
| 6,894,144 B1 | | 5/2005 | Zech et al. | |
| 2002/0058725 A1 | | 5/2002 | Watanabe et al. | |
| 2006/0213396 A1 | | 9/2006 | Kamohara et al. | |
| 2011/0046262 A1 | * | 2/2011 | Bublewitz | A61K 6/18 523/121 |
| 2013/0220172 A1 | * | 8/2013 | Nagasawa | A61K 6/90 106/35 |

FOREIGN PATENT DOCUMENTS

| | | |
|---|---|---|
| EP | 0086062 | 8/1983 |
| JP | H05-025014 | 2/1993 |
| JP | H06-032709 | 2/1994 |
| JP | 2002-087922 | 3/2002 |
| JP | 2003-508470 | 3/2003 |
| JP | 2004-269385 | 9/2004 |
| JP | 2006-273720 | 10/2006 |
| JP | 2011-241198 | 12/2011 |
| JP | 2012-153633 | 8/2012 |
| JP | 2013-095655 | 5/2013 |
| WO | 2014/050028 | 4/2014 |

OTHER PUBLICATIONS

International Search Report for PCT/JP2016/085803 dated Jan. 24, 2017.
Database Epodoc [Online] European Patent Office, The Hague, NL; Jul. 16, 1992 (Jul. 16, 1992), Akamatsu Yasuo et al.: "Curing Agent for Impression Material", XP002796104.

* cited by examiner

*Primary Examiner* — Michael F Pepitone
(74) *Attorney, Agent, or Firm* — IPUSA, PLLC

(57) ABSTRACT

According to an aspect of the present invention, a dental alginate impression material includes an alginate, calcium sulfate, and an aminocarboxylic acid compound.

5 Claims, No Drawings

DENTAL ALGINATE IMPRESSION MATERIAL

The present application is based on and claims the benefit of priority of Japanese Patent Application No. 2016-056593 filed on Mar. 22, 2016, the entire contents of which are herein incorporated by reference.

TECHNICAL FIELD

The present invention relates to a dental alginate impression material.

BACKGROUND ART

In dentistry, the agar-alginate combination impression technique is widely used as a technique for obtaining an impression of the oral cavity when preparing a prosthesis. An agar impression material is primarily used together with an alginate impression material in the one-step combination impression technique. Specifically, an agar impression material that has been liquefied and tempered to a low viscosity state is injected into a portion of the mouth where a cavity is formed after which a tray loaded with a highly viscous alginate impression material is placed in the mouth to obtain an impression.

However, because an agar impression material is a thermo-reversible gel, its initial setting time is short and working time is limited.

On the other hand, alginate impression materials may be a powder-liquid type or a two-paste type (e.g., see Patent Documents 1-5).

PRIOR ART DOCUMENTS

Patent Documents

Patent Document 1: Japanese Unexamined Patent Publication No. 2006-273720
Patent Document 2: Japanese Unexamined Patent Publication No. 2002-87922
Patent Document 3: Japanese Unexamined Patent Publication No. 2004-269385
Patent Document 4: Japanese Unexamined Patent Publication No. 2013-95655
Patent Document 5: Japanese Unexamined Patent Publication No. 2012-153633

SUMMARY OF THE INVENTION

Problem to be Solved by the Invention

There is a demand for improving the storage stability of alginate impression materials.

In this respect, one aspect of the present invention is directed to providing a dental alginate impression material with a long working time and high storage stability.

Means for Solving the Problem

According to one aspect of the present invention, a dental alginate impression material includes an alginate, calcium sulfate, and an aminocarboxylic acid compound.

Advantageous Effect of the Invention

According to an aspect of the present invention, a dental alginate impression material with a long working time and high storage stability may be provided.

Embodiment for Implementing the Invention

In the following, embodiments of the present invention will be described.

A dental alginate impression material includes an alginate, calcium sulfate, and an aminocarboxylic acid compound. In this way, storage stability of the dental alginate impression material may be improved. This may be because the molecular weight of the alginate can be prevented from continually decreasing.

The alginate is not particularly limited as long as it is water-soluble, but for example, sodium alginate, potassium alginate, ammonium alginate, triethanol ammonium, or a combination of two or more of the above substances may be used.

The calcium sulfate is not particularly limited, but for example, calcium sulfate anhydrous, calcium sulfate α hemihydrate, calcium sulfate β hemihydrate, calcium sulfate dehydrate, or a combination of two or more of the above substances may be used. In particular, α-calcium sulfate hemihydrate is preferably used in terms of securing adequate compressive strength of the cured product.

The aminocarboxylic acid compound is not particularly limited, but for example, an aminocarboxylic acid, a metal salt of an aminocarboxylic acid, or a combination of two or more of these substances may be used.

Aminocarboxylic acids include aminomonocarboxylic acids and complexanes (aminopolycarboxylic acids).

Examples of aminomonocarboxylic acids include N,N-bis(2-hydroxyethyl)glycine (DHEG) and N,N-bis(phosphonomethyl)glycine.

Examples of complexanes include aminodiacetic acid (IDA), N-methyliminodiacetic acid (MIDA), N-cyclohexyliminodiacetic acid, uramyl-N, N-diacetic acid, N-phenyldiacetic acid, benzylamino-N,N-diacetic acid, N-(2-furylmethyl)iminodiacetic acid, N-(2-tetrahydropyranylmethyl)iminodiacetic acid, 2-aminomethylpyridine-N,N-diacetic acid, N-(2-methoxyethyl)iminodiacetic acid, N-(2-methylthioethyl)iminodiacetic acid, N-2-hydroxyethyliminodiacetic acid, N-(3-hydroxypropyl)iminodiacetic acid, N-(2-hydrocyclohexyl)iminodiacetic acid, N-(o-hydroxyphenyl)iminodiacetic acid, o-hydroxybenzylamine-N,N-diacetic acid, N-2-mercaptoethyliminodiacetic acid, N-(o-mercaptophenyl)iminodiacetic acid, N-cyanomethyliminodiacetic acid, N-(2-aminoethyl)iminodiacetic acid, ethylenediamine-N,N-diacetic acid, N-(carbamoylmethyl)iminodiacetic acid, (acetamido)iminodiacetic acid, aminoacetone-N,N-diacetic acid, 1-aminopropan-2-one-N,N-diacetic acid, ω-aminoacetophenone-N,N-diacetic acid, N-(o-carboxyphenyl)iminodiacetic acid, nitrilotriacetic acid (NTA), nitrilodiacetic acid methylenesulfonic acid, N-phosphonomethyliminodiacetic acid, nitriloacetic acid-di(methylenesulfonic acid), ethylenediamine-N,N'-diacetic acid (EDDA), ethylenediamine-N,N'-di-α-propionic acid, ethylenediamine-N,N'-di-C-methylacetic acid, ethylenediamine-N,N-dipropionic acid (EDDP), N,N-ethylenebis(α-o-hydroxyphenyl)glycine (EHPG), N,N'-bis(2-hydroxybenzyl)ethylenediamine-N,N'-diacetic acid, ethylenedinitrilo-N,N'-bis(2-hydroxybenzyl)-N,N'-diacetic acid, N,N'-ethylenebis(2-aminomethylpyridine)-N,N'-diacetic acid, ethylenediinitrilo-N,N'-bis(2'-pyridinemethyl)-N,N'-diacetic acid, ethylenediamine-N,N'-diacetic acid-N,N'-diacetohydroxamic acid (EDTA-DX), N-butylethylenediamine-N,N',N'-triacetic acid, N-cyclohexylethylenediamine-N,N',N'-triacetic acid, N-octylethylenediamine-N,N',N'-triacetic acid, N-eicosylethylenediamine-N,N',N'-triacetic acid, N-benzylethylenediamine-N,N',N'-triacetic acid, N-hydroxyethylethylenediamine-N,N',N'-triacetic acid (HEDTA), ethylenediamine-N,N,N',N'-tetraacetic acid (EDTA), 1,2-propylenediamine-N,N,N',N'-tetraacetic acid, 1,2-diaminopropyne-N,N,N',N'-tetraacetic acid (C-MeEDTA), d,I-2,3-diaminobutane-N,N,N',N'-tetraacetic acid (d,I-DIMEDTA), meso-2,3-diaminobutane-N,N,N',N'-tetraacetic acid (meso-DIMEDTA), 1-phenylethylenediamine-N,N,N',N'-tetraacetic acid (C-PhEDTA), d,I-1,2-diphenylethylenediamine-N,N,N',N'-tetraacetic acid (d,I-DPEDTA), 1,3-diaminopropane-N,N,N',N'-tetraacetic acid, 1,4-diaminobutane-N,N,N',N'-tetraacetic acid, tetramethylenediaminetetraacetic acid (TETA), 1,5-diaminopentane-N,N,N',N'-tetraacetic acid, 1,6-diaminohexane-N,N,N',N'-tetraacetic acid, 1,8-diaminooctane-N,N,N',N'-tetraacetic acid, trans-cyclobutane-1,2-diamine-N,N,N',N'-tetraacetic acid (CBDTA), trans-cyclopentane-1,2-diamine-N,N,N',N'-tetraacetic acid (trans-CPDTA), trans-cyclohexane-1,2-diamine-N,N,N',N'-tetraacetic acid (trans-CyDTA), cis-cyclohexane-1,2-diamine-N,N,N',N'-tetraacetic acid (cis-CyDTA), cyclohexane-1,3-diamine-N,N,N',N'-tetraacetic acid (1,3-CyDTA), cyclohexane-1,4-diamine-N,N,N',N'-tetraacetic acid (1,4-CyDTA), o-phenylenediamine-N,N,N',N'-tetraacetic acid (o-PDTA), cis-1,4-diaminobutene-N,N,N',N'-tetraacetic acid (cis-BDTA), trans-1,4-diaminobutene-N,N,N',N'-tetraacetic acid (trans-BDTA), α,α'-diamino-o-xylene-N,N,N',N'-tetraacetic acid (o-XyDTA), 2-hydroxy-1,3-1,3-propanediamine-N,N,N',N'-tetraacetic acid (HPDTA), 2,2'-oxybis(ethyliminodiacetic acid), ethyl ether diamine-N,N,N',N'-tetraacetic acid (EEDTA), 2,2'-ethylenedioxybis(ethyliminodiacetic acid), glycol ether diamine-N,N,N',N'-tetraacetic acid (GEDTA), 3,3'-oxybis(propyliminodiacetic acid), propyl ether diamine-N,N,N',N'-tetraacetic acid, 2,2'-(ethyliminodiacetic acid), ethylthioetherdiamine-N,N,N',N'-tetraacetic acid, 2,2'-ethylenebisthio(ethyliminodiacetic acid), glycolthioetherdiamine-N,N,N',N'-tetraacetic acid, N,N'-glycylethylenediamine-N''',N''',N'''',N''''-tetraacetic acid, ethylenediamine-N,N'-diacetic acid-N,N'-di-α-propionic acid (EDDADP), ethylenediamine-N,N'-diacetic acid-N,N'-di-β-propionic acid (EDPA), ethylenediamine-N,N,N',N'-tetrapropionic acid (EDTP), ethylenediamine-N,N'-bis(acetylglycine)-N,N'-diacetic acid, ethylenediamine-N,N'-diacetic acid-N,N'-bis(methylenephosphonic acid), diethylenetriamine-N,N,N',N'',N''-pentaacetic acid (DTPA), triethylenetetramine-N,N,N',N'',N''',N'''-hexaacetic acid (TTHA), 1,2,3-triaminopropane-N,N,N',N',N'',N''-hexaacetic acid (TAPHA), and the like.

Among the above-mentioned aminocarboxylic acids, in terms of cost and availability of the aminocarboxylic acids for use as dental alginate impression materials, N,N-bis(2-hydroxyethyl)glycine (DHEG), ethylenediamine-N,N,N',N'-tetraacetic acid (EDTA), diethylenetriamine-N,N,N',N'',N''-pentaacetic acid (DTPA), trans-cyclohexane-1,2-diamine-N,N,N',N'-tetraacetic acid (trans-CyDTA), cis-cyclohexane-1,2-diamine-N,N,N',N'-tetraacetic acid (cis-CyDTA), cyclohexane-1,3-diamine-N,N,N',N'-tetraacetic acid (1,3-CyDTA), cyclohexane-1,4-diamine-N,N,N',N'-tetraacetic acid (1,4-CyDTA), N-hydroxyethylethylenediamine-N,N',N'-triacetic acid (HEDTA), triethylenetetramine-N,N,N',N'',N''',N'''-hexaacetic acid (TTHA), and glycol ether diamine-N,N,N',N'-tetraacetic acid (GEDTA) are preferably used.

The aminocarboxylic acid is preferably water-soluble.

Examples of aminocarboxylic acids that are water-soluble include metal salts of aminocarboxylic acids.

Examples of the metal salts include alkali metal salts such as sodium salt, lithium salt and potassium salt.

The dental alginate impression material may be either a one-material type or a two-material type, but in terms of impression accuracy, the two-material type is preferable.

[Two-Material Type]

The dental alginate impression material includes a main material containing an alginate, an aminocarboxylic acid compound, and water; and a hardening material containing calcium sulfate and a nonaqueous dispersion medium.

[Main Material]

The content of the alginate in the main material is normally in a range from 3% to 10% by mass, and is preferably in a range from 5% to 8% by mass. When the content of the alginate in the main material is greater than or equal to 3% by mass, the compressive strength of the cured product can be improved, and when the content of the alginate in the main material is less than or equal to 10%, the impression accuracy can be improved.

The content of the aminocarboxylic acid compound in the main material is normally in a range from 0.01% to 2% by mass, and is preferably in a range from 0.05% to 0.5% by mass. When the content of the aminocarboxylic acid compound in the main material is greater than or equal to 0.01%, the storage stability of the dental alginate impression material can be improved, and when the content of the aminocarboxylic acid compound in the main material is less than or equal to 2% by mass, the compressive strength of the cured product can be improved.

The viscosity of the main material at 23° C. is normally in a range from 4 Pa·s to 40 Pa·s, and is preferably in a range from 5 Pa·s to 35 Pa·s. When the viscosity of the main material at 23° C. is greater than or equal to 4 Pa·s, the compressive strength of the cured product can be improved. When the viscosity of the main material at 23° C. is less than or equal to 40 Pa·s, the impression accuracy can be improved.

The main material preferably further contains a hardening retarder. In this way, the working time can be controlled.

The hardening retarder is not particularly limited, but for example, sodium pyrophosphate or the like may be used.

The main material may further contain a nonionic surfactant, for example.

The nonionic surfactant is not particularly limited, but for example, polyoxyalkylene alkyl ether or the like may be used.

[Hardening Material]

The nonaqueous dispersion medium is not particularly limited as long as it does not react with calcium sulfate, but for example, hydrocarbon, such as decane, undecane, dodecane, tetradecane, kerosene, 1-octene, cycloheptane, cyclononane, liquid paraffin, or polybutene; aliphatic alcohol, such as 1-hexanol, 1-octanol, citronellol, or oleyl alcohol; cyclic alcohol, such as benzyl alcohol, or meta-cresol; fatty acid, such as hexanoic acid, octanoic acid, oleic acid, or linoleic acid, or an ester thereof; polyethylene glycol; polypropylene glycol; or a combination of two or more of the above substances may be used. Among the above-mentioned substances, polyether having at least three hydroxyl groups is preferably used in terms of compatibility.

Examples of the polyether having at least three hydroxyl groups include glycerol propoxylate, trimethylolpropane propoxylate, sorbitol propoxylate, glycerol ethoxylate propoxylate, trimethylol propane ethoxylate, sucrose propoxylate, and the like. Among the above-mentioned substances, glycerol propoxylate is preferably used.

The viscosity of the polyether having at least three hydroxyl groups at 23° C. is normally in a range from 100 mPa·s to 4000 mPa·s, and is preferably in a range from 200 mPa·s to 1000 mPa·s.

Polyethers having at least three hydroxyl groups that are on the market include, for example, Adeka G series, Adeka T series, Adeka SP series, Adeka AM series, Adeka GM series, Adeka R series (all manufactured by Adeka Corporation).

The content of calcium sulfate in the hardening material is normally in a range from 65% to 85% by mass, and is preferably in a range from 70% to 80% by mass. When the content of calcium sulfate in the hardening material is greater than or equal to 65% by mass, the compressive strength of the cured product can be improved, and when the content of calcium sulfate in the hardening material is less than or equal to 85% by mass, the impression accuracy can be improved.

The viscosity of the hardening material at 23° C. is normally in a range from 4 Pa·s to 40 Pa·s, and is preferably in a range from 5 Pa·s to 35 Pa·s. When the viscosity of the hardening material at 23° C. is greater than or equal to 4 Pa·s, the compressive strength of the cured product can be improved, and when the viscosity of the hardening material at 23° C. is less than or equal to 40 Pa·s, the impression accuracy can be improved.

The hardening material preferably further contains a zinc oxide having a number average particle diameter that is less than or equal to 100 nm. In this way, the compressive strength of the cured product can be improved.

The hardening material may further contain a pH adjusting agent, a hardening accelerator, a dispersion stabilizer, and the like.

The pH adjusting agent is not particularly limited, but for example, magnesium hydroxide, magnesium oxide, or the like may be used.

The hardening accelerator is not particularly limited, but for example, glucono delta lactone, lactic acid, citric acid, potassium fluorotitanate, sodium fluorotitanate, or the like may be used.

The dispersion stabilizer is not particularly limited, but for example, fumed silica or the like may be used.

The volume ratio of the hardening material to the main material is normally in a range from 0.25 to 0.5, and is preferably in a range from 0.4 to 0.5. In this way, the compressive strength of the cured product can be improved.

[One-Material Type]

The content of alginate in the dental alginate impression material is normally in a range from 7% to 15% by mass, and is preferably in a range from 10% to 14% by mass. When the content of alginate in the dental alginate impression material is greater than or equal to 7% by mass, the compressive strength of the cured product can be improved, and when the content of alginate in the dental alginate impression material is less than or equal to 15% by mass, the impression accuracy can be improved.

The content of the aminocarboxylic acid compound in the dental alginate impression material is normally in a range from 0.01% to 2% by mass, and is preferably in a range from 0.05% to 0.5% by mass. When the content of the aminocarboxylic acid compound in the dental alginate impression material is greater than or equal to 0.01% by mass, the storage stability of the dental alginate impression material can be improved, and when the content of the aminocarboxylic acid compound in the dental alginate impression material is less than or equal to 2% by mass, the compressive strength of the cured product can be improved.

The content of calcium sulfate in the dental alginate impression material is normally in a range from 12% to 45% by mass, and is preferably in a range from 15% to 40% by mass. When the content of calcium sulfate in the dental alginate impression material is greater than or equal to 12% by mass, the compressive strength of the cured product can be improved, and when the content of calcium sulfate in the dental alginate impression material is less than or equal to 45% by mass, the impression accuracy can be improved.

The dental alginate impression material preferably further contains a zinc oxide having a number average particle diameter that is less than or equal to 100 nm. In this way, the compressive strength of the cured product can be improved.

The dental alginate impression material preferably further contains a hardening retarder. In this way, the storage stability of the dental alginate impression material can be improved.

The hardening retarder is not particularly limited, but for example, sodium pyrophosphate or the like may be used.

The dental alginate impression material may further contain a liquid component, a nonionic surfactant, a pH adjusting agent, a hardening accelerator, a filler and the like.

The liquid component is not particularly limited, but for example, liquid paraffin or the like may be used.

The nonionic surfactant is not particularly limited, but for example, polyoxyalkylene alkyl ether or the like may be used.

The pH adjusting agent is not particularly limited, but for example, magnesium hydroxide, magnesium oxide, or the like may be used.

The hardening accelerator is not particularly limited, but for example, glucono delta lactone, lactic acid, citric acid, potassium fluorotitanate, sodium fluorotitanate, or the like may be used.

The filler is not particularly limited, but for example, diatomaceous earth or the like may be used.

EXAMPLES

In the following, the present invention will be described in detail by way of examples and comparative examples. Note, however, that the present invention is not limited to these examples.

[Two-Material Type]

Examples 1-1 to 1-11, Comparative Examples 1-1 to 1-4

Alginate, trisodium ethylenediaminetetraacetate (EDTA·3Na), polyoxyalkylene alkyl ether (POAAE), and sodium pyrophosphate were mixed together at the mix ratios indicated in Table 1 below to obtain the main material.

Calcium sulfate, glycerol propoxylate, zinc oxide powder, magnesium hydroxide, potassium fluorotitanate, and fumed silica were mixed together at the mix ratios indicated in Table 1 to obtain the hardening material.

The following is information on the raw materials listed in Table 1.

Sodium alginate: Duck Algin NSPM (manufactured by Kikkoman Biochemifa Co., Ltd.)

Potassium alginate: Duck Algin K (manufactured by Kikkoman Biochemifa Co., Ltd.)

POAAE: Naroacty CL (manufactured by Sanyo Chemical Industries, Ltd.)

Glycerol propoxylate: G-300 (manufactured by Adeka Corporation)

Zinc oxide powder A: number average particle diameter 20 nm

Zinc oxide powder B: number average particle diameter 100 nm

Also, the method of measuring the number average particle diameter of the zinc oxide powder is described below.

<Number Average Particle Diameter of Zinc Oxide Powder>

The number average particle diameter of the zinc oxide powder was measured by a laser dynamic light scattering analyzer ELS-Z (manufactured by Otsuka Electronics Co., Ltd.) using water as a dispersion medium.

Next, the viscosities of the main material and the hardening material were measured.

<Viscosity of Main Material and Hardening Material>

The viscosities of the main material and the hardening material at 23° C. were measured using an E type viscometer RE-85 (manufactured by Toki Sangyo Co., Ltd.), under conditions where the cone angle was 3° and the shear rate was 24 s$^{-1}$ (rotational speed was 12 rpm).

Next, the compression strength of the cured product, the initial setting time, the storage stability of the main material, and the impression accuracy were evaluated.

<Compressive Strength of Cured Product>

The main material and the hardening material were weighted out on kneader paper at volume ratio indicated in Table 1 and kneaded for 30 seconds with a spatula, and the compressive strength of the cured product was measured according to JIS T6505.

<Initial Setting Time>

The main material and the hardening material were weighed out on kneader paper at the volume ratio indicated in Table 1 and kneaded for 30 seconds with a spatula, and the initial setting time was measured according to JIS T6505. Note that the measurement of the initial setting time was performed in 5-second units.

<Storage Stability of Main Material>

After storing the main material for 1 week in an environment of 60° C. and 100% RH, the viscosity of the main material at 23° C. was measured in the same manner as described above. Then, the rate of change in the viscosity of the main material was calculated using the following formula:

[(Viscosity After Storage)−(Initial Viscosity)]/(Initial Viscosity)×100

<Impression Accuracy>

The main material and the hardening material were weighed out on kneaded paper at the volume ratio indicated in Table 1 and kneaded for 30 seconds with a spatula, and the impression accuracy was evaluated by the compatibility test with gypsum according to JIS T 6505.

Table 1 indicates the evaluation results of the compressive strength of the cured product, the initial setting time, the storage stability of the main material, and the impression accuracy.

TABLE 1

UNIT OF MIX RATIO: MASS %

| | | EXAMPLE 1 | | | | | | | | | | | COMPARATIVE EXAMPLE 1 | | | |
|---|---|---|---|---|---|---|---|---|---|---|---|---|---|---|---|---|
| | | 1 | 2 | 3 | 4 | 5 | 6 | 7 | 8 | 9 | 10 | 11 | 1 | 2 | 3 | 4 |
| MAIN MATERIAL | SODIUM ALGINATE | | | 6 | 3 | | | | | | | | | | | | |
| | POTASSIUM ALGINATE | 6 | 6 | | 3 | 3 | 10 | 6 | 6 | 6 | 6 | 6 | 2 | 11 | 6 | 6 |
| | WATER | 91.8 | 91.8 | 91.8 | 91.8 | 94.89 | 85.97 | 91.8 | 91.8 | 91.8 | 91.8 | 91.8 | 95.9 | 86.9 | 91.9 | 91.9 |
| | EDTA•3Na | 0.1 | 0.1 | 0.1 | 0.1 | 0.01 | 2 | 0.1 | 0.1 | 0.1 | 0.1 | 0.1 | | | | |
| | POAAE | 2 | 2 | 2 | 2 | 2 | 2 | 2 | 2 | 2 | 2 | 2 | 2 | 2 | 2 | 2 |
| | SODIUM PYROPHOSPHATE | 0.1 | 0.1 | 0.1 | 0.1 | 0.1 | 0.03 | 0.1 | 0.1 | 0.1 | 0.1 | 0.1 | 0.1 | 0.1 | 0.1 | 0.1 |
| | TOTAL | 100 | 100 | 100 | 100 | 100 | 100 | 100 | 100 | 100 | 100 | 100 | 100 | 100 | 100 | 100 |
| HARDENING MATERIAL | α-CALCIUM SULFATE HEMIHYDRATE | 70 | 70 | 70 | 70 | 70 | 70 | 85 | 65 | 70 | 70 | 70 | 70 | 70 | 90 | 60 |
| | GLYCEROL PROPOXYLATE | 25 | 25 | 25 | 25 | 25 | 25 | 13 | 26 | 21 | 25 | 25 | 25 | 25 | 8 | 31 |
| | ZINC OXIDE POWDER A | | 1 | | | | | | | | 0.1 | | | | | |
| | ZINC OXIDE POWDER B | | | | | | | | | 5 | | | | | | |
| | MAGNESIUM HYDROXIDE | 1 | 1 | 1 | 1 | 1 | 1 | 1 | 1 | 1 | 1 | 1 | 1 | 1 | 1 | 1 |
| | POTASSIUM FLUOROTITANATE | 2 | 2 | 2 | 2 | 2 | 2 | 0.5 | 2 | 2 | 2 | 2 | 2 | 2 | 0.5 | 2 |
| | FUMED SILICA | 2 | 1 | 2 | 2 | 2 | 2 | 0.5 | 6 | 1 | 1.9 | 2 | 2 | 2 | 0.5 | 6 |
| | TOTAL | 100 | 100 | 100 | 100 | 100 | 100 | 100 | 100 | 100 | 100 | 100 | 100 | 100 | 100 | 100 |
| | MAIN MATERIAL VISCOSITY [Pa · s] | 5 | 5 | 8 | 5 | 4 | 38 | 5 | 5 | 5 | 5 | 5 | 2 | 51 | 6 | 6 |
| | HARDENING MATERIAL VISCOSITY [Pa · s] | 6 | 7 | 6 | 6 | 6 | 6 | 40 | 6 | 6 | 6 | 6 | 6 | 6 | 62 | 5 |
| | VOLUME RATIO (MAIN MATERIAL:HARDENING MATERIAL) | 4:1 | 4:1 | 4:1 | 4:1 | 4:1 | 4:1 | 4:1 | 4:1 | 4:1 | 4:1 | 4:1 | 2:1 | 4:1 | 4:1 | 4:1 |
| | COMPRESSIVE STRENGTH OF CURED PRODUCT [MPa] | 0.5 | 0.8 | 0.6 | 0.4 | 0.5 | 0.6 | 0.5 | 0.5 | 0.7 | 0.7 | 0.5 | 0.3 | 0.7 | 0.6 | 0.3 |
| | INITIAL SETTING TIME [s] | 90 | 80 | 100 | 90 | 80 | 70 | 90 | 90 | 70 | 75 | 90 | 110 | 60 | 50 | 70 |
| | MAIN MATERIAL STORAGE STABILITY [%] | −5 | −3 | −4 | −6 | −8 | −5 | −7 | −2 | −2 | −4 | −6 | −90 | −96 | −84 | −93 |
| | IMPRESSION ACCURACY [μm] | 20 | 20 | 20 | 20 | 20 | 20 | 20 | 20 | 20 | 20 | 20 | 20 | 50 | 50 | 20 |

It can be appreciated from Table 1 that the alginate impression materials of Examples 1-1 to 1-11 have long initial setting times and their main materials have high storage stability.

In contrast, the alginate impression materials of Comparative Examples 1-1 to 1-4 contain no aminocarboxylic acid, and as a result, their main materials have lower storage stability.

[One-Material Type]

Examples 2-1 to 2-7, Comparative Examples 2-1 to 2-3

Alginate, trisodium ethylenediaminetetraacetate (EDTA·3Na), calcium sulfate, zinc oxide powder, magnesium hydroxide, potassium fluorotitanate, polyoxyalkylene alkyl ether (POAAE), liquid paraffin, sodium pyrophosphate and diatomaceous earth were mixed together at the mix ratio indicated in Table 2 below to obtain the alginate impression material.

Next, the flow value of the alginate impression material was measured.

<Flow Value>

16.8 g of the alginate impression material was weighed out and placed in a rubber cup after which 40 cc of water was weighed out and poured into the rubber cup, and the alginate impression material and water were kneaded for 30 seconds with a spatula to obtain a kneaded material. Next, the kneaded material was filled in a metal ring having an inner diameter of 35 mm and a height of 50 mm, and only the kneaded material was quickly extruded onto a glass plate and cured. The spread of the kneaded material due to its own weight, that is, the diameter of the cured product was measured as a surrogate characteristic of sagability to represent the flow value.

Next, the compressive strength, the initial setting time, the storage stability, and the impression accuracy of the cured product were evaluated.

<Compressive Strength of Cured Product>

16.8 g of the alginate impression material was weighed out and placed in a rubber cup after which 40 cc of water was weighted out and poured into the rubber cup, and the alginate impression material and water were kneaded for 30 seconds with a spatula and cured. The compressive strength of the cured product was measured according to JIS T 6505.

<Initial Setting Time>

16.8 g of the alginate impression material was weighed out and placed in a rubber cup after which 40 cc of water was weighed out and poured into the rubber cup, and the alginate impression material and water were kneaded for 30 seconds with a spatula and cured. The initial setting time of the alginate impression material was measured according to JIS T 6505. Note that the measurement of the initial setting time was performed in 5-second units.

<Storage Stability>

After storing the alginate impression material for 1 week under an environment of 60° C. and 100% RH, the flow value of the alginate impression was measured, and a change in the flow value of the alginate impression material was calculated using the following formula:

(Flow Value After Storage)−(Initial Flow Value)

<Impression Accuracy>

16.8 g of the alginate impression material was weighed out and placed in a rubber cup after which 40 cc of water was weighed out and poured into the rubber cup, the alginate impression material and water were kneaded for 30 seconds with a spatula, and the impression accuracy was evaluated by the compatibility test with gypsum according to JIS T 6505.

Table 2 indicates the evaluation results of the compressive strength of the cured product, the initial setting time, the storage stability, and the impression accuracy.

TABLE 2

UNIT OF MIX RATIO: MASS %

| | EXAMPLE 2 | | | | | | | COMPARATIVE EXAMPLE 2 | | |
|---|---|---|---|---|---|---|---|---|---|---|
| | 1 | 2 | 3 | 4 | 5 | 6 | 7 | 1 | 2 | 3 |
| SODIUM ALGINATE | 12 | 12 | | 6 | 7 | | 12 | 12 | 12 | |
| POTASSIUM ALGINATE | | | 12 | 6 | | 15 | | | | 12 |
| EDTA•3Na | 0.1 | 0.1 | 0.1 | 0.1 | 0.01 | 2 | 0.1 | | | |
| α-CALCIUM SULFATE HEMIHYDRATE | | | 12 | 6 | 8 | 15 | 45 | | | 12 |
| CALCIUM SULFATE DIHYDRATE | 12 | 12 | | 6 | 8 | | | 12 | 12 | |
| ZINC OXIDE POWDER A | | 1 | | | | | | | 1 | |
| MAGNESIUM HYDROXIDE | 1 | 1 | 1 | 1 | 1 | 1 | 1 | 1 | 1 | 1 |
| POTASSIUM FLUOROTITANATE | 1 | 1 | 1 | 1 | 1 | 2 | 1 | 1 | 1 | 1 |
| POAAE | 0.3 | 0.3 | 0.3 | 0.3 | 0.3 | 0.3 | 0.3 | 0.3 | 0.3 | 0.3 |
| LIQUID PARAFFIN | 1 | 1 | 1 | 1 | 1 | 1 | 1 | 1 | 1 | 1 |
| SODIUM PYROPHOSPHATE | 2 | 2 | 2 | 2 | 2 | 0.3 | 2 | 2 | 2 | 2 |
| DIATOMACEOUS EARTH | 70.6 | 69.6 | 70.6 | 70.6 | 71.69 | 63.4 | 37.6 | 70.7 | 69.7 | 70.7 |
| TOTAL | 100 | 100 | 100 | 100 | 100 | 100 | 100 | 100 | 100 | 100 |
| FLOW VALUE [mm] | 52 | 51 | 49 | 50 | 55 | 45 | 58 | 0.5 | 0.8 | 0.6 |
| COMPRESSIVE STRENGTH OF CURED PRODUCT [MPa] | 0.5 | 0.8 | 0.6 | 0.4 | 0.5 | 0.6 | 0.8 | 120 | 80 | 100 |
| INITIAL SETTING TIME [s] | 120 | 130 | 125 | 135 | 140 | 125 | 130 | 51 | 52 | 50 |
| STORAGE STABILITY [mm] | +2 | +3 | +1 | +5 | +2 | +2 | +4 | +22 | +15 | +18 |
| IMPRESSION ACCURACY [μm] | 50 | 20 | 20 | 20 | 20 | 20 | 50 | 50 | 20 | 20 |

It can be appreciated from Table 2 that the alginate impression materials of Examples 2-1 to 2-7 have long initial setting times and high storage stability.

In contrast, the alginate impression materials of Comparative Examples 2-1 to 2-3 contain no aminocarboxylic acids and therefore have lower storage stability.

The invention claimed is:

1. A dental alginate impression material comprising:
   a main material including an alginate, an aminocarboxylic acid compound, and water; and
   a hardening material including calcium sulfate and a nonaqueous dispersion medium, wherein
   the nonaqueous dispersion medium is a polyether having at least three hydroxyl groups, the polyether having at least three hydroxyl groups having a viscosity at 23° C. in a range from 100 mPa·s to 4000 mPa·s.

2. The dental alginate impression material according to claim 1, wherein
   the main material contains the alginate at a content ranging from 3% to 10% by mass and contains the aminocarboxylic acid compound at a content ranging from 0.01% to 2% by mass; and
   the hardening material contains the calcium sulfate at a content ranging from 65% to 85% by mass.

3. The dental alginate impression material according to claim 1, wherein the main material and the hardening material each have viscosities ranging from 4 Pa·s to 40 Pa·s at 23° C.

4. The dental alginate impression material according to claim 1, wherein the hardening material further includes a zinc oxide having a number average particle diameter that is less than or equal to 100 nm.

5. The dental alginate impression material according to claim 1, wherein a volume ratio of the hardening material with respect to the main material is from 0.25 to 0.5.

* * * * *